United States Patent [19]

Petrzilka

[11] 4,419,262
[45] Dec. 6, 1983

[54] PYRIDAZINES

[75] Inventor: Martin Petrzilka, Kaiseraugst, Switzerland

[73] Assignee: Hoffmann-La Roche Inc., Nutley, N.J.

[21] Appl. No.: 396,998

[22] Filed: Jul. 12, 1982

[30] Foreign Application Priority Data

May 14, 1982 [CH] Switzerland .................. 3014/82

[51] Int. Cl.$^3$ .............. C09K 3/34; C02F 1/13; C07D 237/08; C07D 237/02
[52] U.S. Cl. ................ 252/299.61; 252/299.5; 252/299.63; 252/299.67; 350/346; 350/350 R; 544/224
[58] Field of Search ............ 544/224; 252/299.61, 252/299.67, 299.63, 299.5; 350/350, 396

[56] References Cited

U.S. PATENT DOCUMENTS

| | | | |
|---|---|---|---|
| 3,997,536 | 12/1976 | Boller et al. | 252/299.61 |
| 4,062,798 | 12/1977 | Boller et al. | 252/299.61 |
| 4,273,929 | 6/1981 | Boller et al. | 252/299.1 |
| 4,309,539 | 1/1982 | Boller et al. | 252/299.1 |
| 4,323,473 | 4/1982 | Sethofer | 252/299.61 |
| 4,335,011 | 6/1982 | Sethofer | 252/299.61 |
| 4,344,856 | 8/1982 | Demus et al. | 252/299.61 |
| 4,348,298 | 9/1982 | Zaschke et al. | 252/299.61 |
| 4,358,589 | 11/1982 | Schubert et al. | 252/299.1 |
| 4,364,838 | 12/1982 | Boller et al. | 252/299.61 |

FOREIGN PATENT DOCUMENTS

| | | |
|---|---|---|
| 36711 | 9/1981 | European Pat. Off. |
| 56501 | 7/1982 | European Pat. Off. ........ 252/299.61 |
| 2257588 | 6/1973 | Fed. Rep. of Germany .................. 252/299.61 |
| 2835492 | 2/1980 | Fed. Rep. of Germany |
| 2085877 | 5/1982 | United Kingdom ........... 252/299.61 |

OTHER PUBLICATIONS

Boller, A., et al., Mol. Cryst. Liq. Cryst., vol. 42, No. 1–3, pp. 215–231 (1977).
Nash, J. A., et al., Mol. Cryst. Liq. Cryst., vol. 25, pp. 299–321 (1974).
Schubert, Hermann, Wiss. Z. Univ. Halle, XIX'70 M, H. S. 5.1–18.
Dabrowski, R., et al., Mol. Cryst. Liq. Cryst., vol. 87, pp. 109–135 (1982).
C. A., 96: 103527p (1982).
C. A., 66: 54977e (1967).
Ohsawa, A., et al., Chem. Pharm. Bull., vol. 28, pp. 3488–3493 (1980).
Schubert, H., et al., Z. Chemie, vol. 6, pp. 467 (1966) C. A. 88: 6824k (1978).
Weygand, C., et al., J. Prakt. Chemie, vol. 151, pp. 221–227 (1938).
C. A., 10: 1534 (1939).
Zaschke, H., et al., Z. Chemie, vol. 17, pp. 333–334, (1977).

Primary Examiner—Teddy S. Gron
Attorney, Agent, or Firm—Jon S. Saxe; Bernard S. Leon; George W. Johnston

[57] ABSTRACT

Compounds of the formula

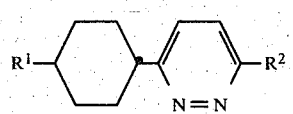

wherein $R^1$ is straight-chain alkyl of 1 to 12 carbon atoms, $R^2$ is 1-alkynyl and the 1-alkynyl group in $R^2$ is a straight-chain group of 1 to 10 carbon atoms, their manufacture, liquid crystalline mixtures containing said compounds as well as their use for electro-optical purposes are described. The novel compounds are valuable components for liquid crystalline mixtures and have a negative dielectric anisotropy.

15 Claims, No Drawings

PYRIDAZINES

BACKGROUND OF THE INVENTION

1. Field of the Invention

This invention relates to liquid crystalline compounds and mixtures.

2. Description of the Prior Art

In an electric field, the molecules of liquid crystalline nematic and cholesteric compounds or mixtures which possess a negative anisotropy of the dielectric constants (i.e. $\epsilon_{81} < \epsilon_\perp$) are oriented with their longitudinal axes perpendicular to the field direction. $\epsilon_\parallel$ signifies the dielectric constant along the longitudinal axis of the molecule and $\epsilon_\perp$ signifies the dielectric constant perpendicular thereto.

This dielectric field effect is used for the control of the optical transmissivity in various liquid crystal indicators. For example, the effect is utilized in liquid crystal cells of the light scattering type (dynamic scattering), of the so-called DAP type or of the guest-host type [guest-host interaction; Applied Physics Letters 13 (1968) 91].

These "guest-host cells" comprise essentially a condenser-like structure with at least one electrode plate being transparent and a dielectric being formed from nematic or cholesteric liquid crystal materials which contain one or more dichoric dyes. In the cells, the longitudinal axes of these colouring substances and the liquid crystals align parallel to each other. Since the colouring substances usually have positive dichorism, their transition moment of the absorption of visible light lies approximately in the direction of the longitudinal molecular axis of the dye. That is, one sees a colour when viewing in a direction perpendicular to the longitudinal axis of the dyes. Consequently, the orientation of the liquid crystal and dyes with their molecular axes parallel to the surface of the plates generally corresponds to the coloured state. Also, the homeotropic orientation (longitudinal molecular axes perpendicular to the surface of the plates) generally corresponds to the colourless condition of the cell.

When a liquid crystal with positive dielectric anisotropy is used ($\epsilon_\parallel > \epsilon_\perp$), its homogeneous orientation (i.e. longitudinal axis of molecules is parallel to surface of electrode, which is achieved by suitably treating the surface of the electrode plates) becomes homeotropic (i.e. longitudinal axis of molecules is perpendicular to surface of the electrodes) by the application of a voltage. Consequently, from the field-off to the field-on state, the cell is switched from "coloured" to "colourless". In this manner, colourless symbols are shown on a coloured background. With a liquid crystal having negative dielectric anisotropy ($\epsilon_\parallel < \epsilon_\perp$), its homeotropic orientation (i.e. by suitably treating the surface of the electrode plates) is arranged parallel to the electrode surfaces by the application of a voltage. Thus, with the field-on state there results a coloured image elements on a colourless background.

Further, for the improvement of the multiplex ratio in the multiplex control of liquid crystal indicators (especially of rotation cells and guest-host cells), there has been proposed a two-frequency matrix addressing procedure (e.g German Offenlegungsshchriften Nos. 28 56 134 (Great Britain Pat. No. 2,013,014) and 29 07 940 (Great Britain Pat. No. 2,020,075)). This procedure makes use of the fact that the dielectric anisotropy of nematic liquid crystals having a positive anisotropy of the dielectric constants upon application of a low-frequency voltage, is negative in the case of high frequencies. To maintain a relatively low energy consumption, the "cross-over frequency" $f_c$ (dielectric relaxation frequency at which $\delta_\parallel = \epsilon_\perp$) of such liquid crystals should be at most 20 kHz or smaller. Further, the absolute dielectric anisotropies should be as large as possible not only below but also above the cross-over frequency. Disadvantageously, at frequencies above the cross-over frequency, the substances which are especially suitable for the two-frequency procedure generally have a smaller absolute dielectric anisotropy than below the cross-over frequency. Tnhis disadvantage, however, can be eliminated by addng one or more compounds with negative dielectric anisotropy and establishing suitable relaxation behavior.

Furthermore, liquid crystals which in the case of high frequencies have a negative dielectric anisotropy can, however, also be controlled by switching-on and switching-off an alternating current of high frequency. The liquid crystals thereby behave as customary liquid crystals with negative anisotropy of the dielectric constants.

A series of liquid crystalline compounds with weakly negative dielectric anisotropy has already hitherto been synthesized. However, still relatively few liquid crystals with large negative anisotropy of the dielectric constants are known. Moreover, the latter generally have disadvantages such as poor solubility in mixtures, high melting points, high viscosity, strong smectic tendencies and chemical instability. These accordingly exists a great need for further improved compounds with negative anisotropy of the dielectric constants which can be utilized in a wide variety of display applications.

SUMMARY OF THE INVENTION

The invention relates to pyridazines of the formula

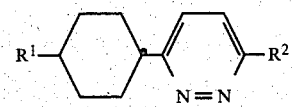

I wherein $R^1$ is straight-chain alkyl of 1 to 12 carbon atoms, $R^2$ is 1-alkynyl and the 1-alkynyl group in $R^2$ is a straight-chain group of 2 to 10 carbon atoms.

It has now been found that the compounds of formula I have a large negative anisotropy of the dielect constants, a good solubility in known liquid crystal mixtures and a relatively low viscosity. Further, they are colourless and have a good chemical stability and only slight smectic tendencies. The compounds provided by the invention are therefore especially suitable for improving the properties of liquid crystal mixtures with negative anisotropy of the dielectric constants or of liquid crystal mixtures which are suitable for two-frequency matrix addressing.

The invention is also concerned with the manufacture of the compounds of formula I above, liquid crystalline mixtures containing such compounds as well as their use in electro-optical devices.

DETAILED DESCRIPTION OF THE INVENTION

The present invention is concerned with novel 6-(trans-4-alkylcyclohexyl)pyridazines of the formula

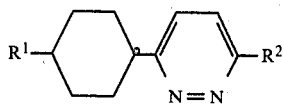

ps wherein $R^1$ is straight-chain alkyl of 1 to 12 carbon atoms, $R^2$ is 1-alkynyl and the 1-alkynyl group in $R^2$ is a straight-chain group of 2 to 10 carbon atoms.

The compounds provided by the invention are valuable as components of liquid crystalline (especially nematic and cholesteric) mixtures and have a negative anisotropy of the dielectric constants. The inventive compounds are soluble in known liquid crystal mixtures and have a relatively low viscosity. Further, they are colourless and have a good chemical stability and only slight smectic tendencies. The compounds provided by the invention are therefore especially suitable for improving the properties of liquid crystal mixtures with negative anisotropy of the dielectric constants or of liquid crystal mixtures which are suitable for two-frequency matrix addressing. However, they can of course also be used in mixtures with positive dielectric anisotropy in order to adapt the threshold potential to the electro-optical cell which is used.

The compound of formula I generally have only monotropic or virtual clearing points. It has, however, surprisingly been found that in mixtures they give only slight clearing point depressions, whereas the melting points can be considerably lowered eutectic.

Unless otherwise stated, "alkyl" denotes a straight-chain alkyl group of 1 to 12 carbon atoms or a branched-chain alkyl group of 1 to 12 carbon atoms. Exemplary straight-chain alkyl groups are methyl, ethyl, propyl, butyl, pentyl, hexyl, heptyl octyl, nonyl, decyl, undecyl and dodecyl. Exemplary branched-chain alkyl groups are isopropyl, isobutyl, sec-butyl, 1-methylbutyl, 2-methylbutyl 3-methylphenyl, 4-methylhexyl and isopentyl. Lower alkyl denotes straight-chain and branched-chain alkyl groups of 1 to 5 carbon atoms. The alkyl group $R^1$ can contain 1 to 12 carbon atoms.

The terms "alkoxy", "alkanoyloxy" and "1-alkynyl" as well as the other groups in the specification containing "alkyl" denote moieties in which their "alkyl" portions are as defined previously. In particular, straight-chain alkoxy groups denote moieties having a straight-chain alkyl portion as previously defined. Moreover, the group $R^2$ of formula I embraces 1-alkynyl groups of 2 to 10 carbon atoms. Exemplary 1-alkynyl groups are ethynyl, 1-propynyl, 1-butynyl and 1-pentynyl.

The term "halogen" denotes fluorine, chlorine, bromine or iodine.

The term "alkali metal" denotes sodium, potassium or lithium.

Preferred compounds of formula I are those in which the 1-alkynyl group in $R^2$ is a straight-chain group of 2 to 7 carbon atoms. Preferred $R^1$ groups are straight-chain alkyl groups containing 3 to 9 carbon atoms and especially those containing 3 to 7 carbon atoms. Accordingly, especially preferred compounds of formula I are those in which $R^1$ represents a straight-chain alkyl group containing 3 to 7 carbon atoms and $R^2$ represents a straight-chain 1-alkynyl group containing 2 to 7 carbon atoms.

The following are examples of preferred compounds of formula I:
3-ethynyl-6-(trans-4-propylcyclohexyl)pyridazine,
3-ethynyl-6-(trans-4-butylcyclohexyl)pyridazine,
3-ethynyl-6-(trans-4-pentylcyclohexyl)pyridazine,
3-ethynyl-6-(trans-4-hexylcyclohexyl)pyridazine,
3-ethynyl-6-(trans-4-heptylcyclohexyl)pyridazine,
3-(1-propynyl)-6-(trans-4-propylcyclohexyl)pyridazine,
3-(1-propynyl)-6-(trans-4-butylcyclohexyl)pyridazine,
3-(1-propynyl)-6-(trans-4-pentylcyclohexyl)pyridazine,
3-(1-propynyl)-6-(trans-4-hexylcyclohexyl)pyridazine,
3-(1-propynyl)-6-(trans-4-heptylcyclohexyl)pyridazine,
3-(1-butynyl)-6-(trans-4-propylcyclohexyl)pyridazine,
3-(1-butynyl)-6-(trans-4-pentylcyclohexyl)pyridazine,
3-(1-butynyl)-6-(trans-4-heptylcyclohexyl)pyridazine,
3-(1-pentynyl)-6-(trans-4-propylcyclohexyl)pyridazine,
3-(1-pentynyl)-6-(trans-4-pentylcyclohexyl)pyridazine, and
3-(1-pentynyl)-6-(trans-4-heptylcyclohexyl)pyridazine.

The compounds of formula I can be manufactured in accordance with the invention by (a) for the manufacture of the compounds of formula I in which $R^2$ represents the ethynyl group, reacting a compound of the formula

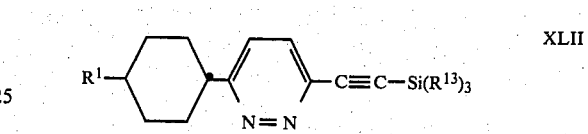

wherein $R^{13}$ is alkyl of 1 to 5 carbon atoms and $R^1$ has the significance given earlier, with a base, or (b) for the manufacture of the compounds of formula I in which $R^2$ represents a 1-alkynyl group containing 3 to 10 carbon atoms, converting a compound of the formula

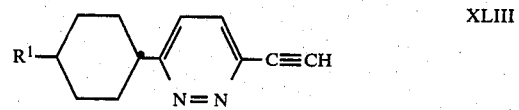

wherein $R^1$ has the significance given earlier, with a base into the corresponding ethynylide and alkylating said ethynylide with an alkyl bromide or alkyl iodide, or (c) for the manufacture of the compounds of formula I in which $R^2$ represents a 1-alkynyl group containing 3 to 10 carbon atoms, reacting a compound of the formula

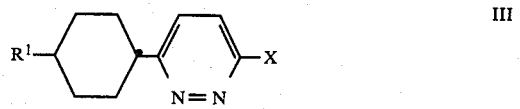

wherein X is chlorine or bromine and $R^1$ has the significance given earlier, in the presence of a triphenylphosphine-palladium compound, copper (I) iodide an amine with a compound of the formula $$R^{14}—C≡C—H \qquad \text{XLIV}$$

wherein $R^{14}$ is straight-chain alkyl of 1 to 8 carbon atoms.

The reaction of a compound of formula XLII with a base in accordance with process variant (a) can be carried out in a manner known per se. Suitable bases are, for example, potassium hydroxide, sodium hydroxide, sodium carbonate, butyl lithium, methyl lithium and the like. $R^{13}$ in formula XLII preferably represents methyl or ethyl. Temperature and pressure are not critical. However, the reaction is preferably carried out at atmospheric pressure and a temperature between about room temperature (23° C.) and the reflux temperature of the reaction mixture.

The compounds of formula XLII can be prepared in a manner known per se from the compounds of formula III. The reaction can be carried out under the conditions described hereinafter for process variant (c) with an ethynyl-trialkylsilane in the presence of a suitable triphenylphosphine-palladium compound, copper (I) iodide and an amine. A compound of formula III in which X represents bromine is preferably used.

The conversion of a compound of formula XLIII into the corresponding ethynylide and the subsequent alkylation with an alkyl bromide or alkyl iodide in accordance with process variant (b) can also be carried out in a manner known per se. Suitable bases are, for example, butyl lithium, methyl lithium, sodium amide, lithium diisopropylamide and the like. The alkylation is preferably carried out with an alkyl iodide. Temperature and pressure are not critical. However, atmospheric pressure and a temperature between about −70° C. and about room temperature (23° C.) are preferably used.

The reaction of a compound of formula III with a compound of formula XLIV in the presence of a triphenylphosphine-palladium compound, copper (I) iodide and an amine in accordance with process variant (c) can be carried out in a manner known per se; for example, in an analogous manner to the reactions described in Chem. Pharm. Bull. 28, 3488 (1980), Synthesis 627 (1980) and J. Org. Chem. 46, 2280 (1981). Suitable triphenylphosphine-palladium compounds are bis-(triphenylphosphine)-palladium (II) dichloride, tetrakis-(triphenylphosphine)-palladium and the like. Examples of suitable bases are triethylamine, piperidine, diethylamine and the like. Tertiary amines are preferred. Temperature and pressure are not critical aspects in this reaction. Atmospheric pressure and a temperature between about room temperature (23° C.) and about 40° C. are preferably used.

The starting materials of formula III are novel and also form objects of the present invention. They can be prepared according to Reaction Schemes A and B hereinafter in which $R^1$ and X have the significances given earlier:

Scheme A

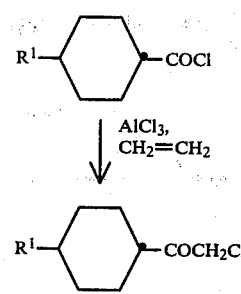

Scheme B

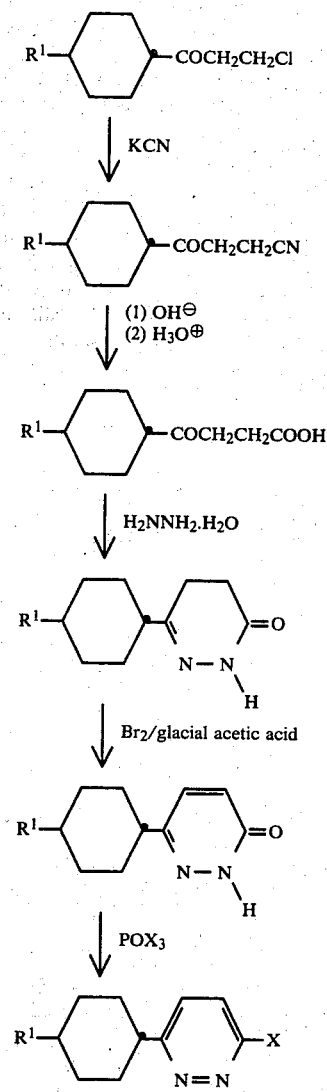

The compounds provided by the invention can be used in the form of mixtures with other liquid crystalline or non-liquid crystalline substances such as, for example, with substances from the classes of Schiffs' bases, azobenzenes, azoxybenzenes, phenyl benzoates, cyclohexanecarboxylic acid phenyl esters and cyclohexyl esters, biphenyls, terphenyls, phenylcyclohexanes, cinnamic acid derivatives, phenylpyrimidines, diphenylpyrimidines, phenylidioxanes, cyclohexylphenylpyrimidines, phenylbicyclo[2.2.2]octanes, 1-phenyl-2-cyclohexylethanes, derivatives of hydroquinone and 4-hydroxybenzoic acid and the like. Such compounds are known to a person skilled in the art and many of them are, moreover, commercially available.

In principle, the compounds provided by the invention can be used in mixtures for any liquid crystal indicators, thus, for example, even in liquid crystal mixtures with positive dielectric anisotropy for the purpose of adjusting the dielectric anisotropies of the mixtures utilized in the cell. The compounds provided by the invention are, however, preferably used in mixtures with negative dielectric anisotropy or in mixtures with frequency-dependent dielectric anisotropy which are suitable for the two-frequency control procedure.

The liquid crystal mixtures provided by the invention for the two-frequency control contain, in addition to one or more compounds of formula I, preferably a nematic matrix with a dielectric anisotropy of about −3 to about +1 and one or more components with low cross-over frequency (about 100 Hz to about 20 kHz) and strongly positive dielectric anisotropy (Δε>10) at frequencies which lie clearly below the cross-over frequency of the total mixture. Preferred examples of the last-mentioned compounds are the phenyl benzoates and diesters of 2-chloro-4-hydroxybenzoic acid disclosed in German Offenlegungsschrift No. 30 26 965 (Great Britain Pat. No. 2,058,050) and especially the p-(2,2-dicyanovinyl)phenyl esters of the formula

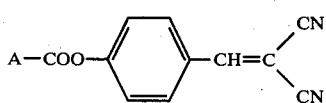

XXII wherein A represents a group of the formula

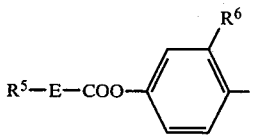

XXIII or a group of the formula

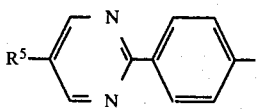

XXIV wherein $R^5$ alone is straight-chain alkyl of 1 to 12 carbon atoms and $R^6$ is fluorine, chlorine, bromine or cyano and $R^5$—E is p-alkylphenyl, trans-4-alkylcyclohexyl, 4'-alkyl-4-biphenylyl, p-(trans-4-alkylcyclohexyl)phenyl or p-(5-alkyl-2-pyrimidinyl)phenyl.

The aforementioned nematic matrix with a dielectric anisotropy of about −3 to about +1 preferably contains one or more of the following compounds:

Trans-4-alkylcyclohexanecarboxylic acid p-alkoxyphenyl esters of the formula

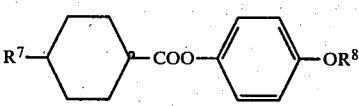

XXV wherein $R^7$ and $R^8$ each are straight-chain alkyl of 1 to 8 carbon atoms, trans-4-alkyl-1-(p-alkylphenyl)cyclohexanes of the formula

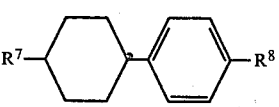

XXVI wherein $R^7$ and $R^8$ are as above,
4,4'-dialkylbiphenyls of the formula

XXVII wherein $R^7$ and $R^8$ are as above,
trans-4-alkylcyclohexanecarboxylic acid trans-4-alkylcyclohexyl esters fo the formula

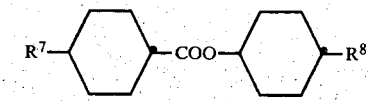

XXVIII wherein $R^7$ and $R^8$ are as above,
p-alkylbenzylidene-p'-alkylanilines of the formula

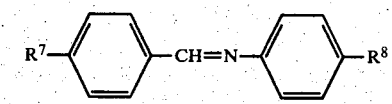

XXIX wherein $R^7$ and $R^8$ are as above,
4-alkyl-1-(p-alkylphenyl)bicyclo[2.2.2]octanes of the formula

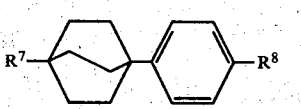

XXX wherein $R^7$ and $R^8$ are as above,
(trans-4-alkylcyclohexyl)ethanes of the formula

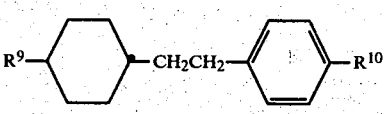

XXXI wherein $R^{10}$ is —$R^{11}$ or —$OR^{11}$ and $R^9$ and $R^{11}$ each are straight-chain alkyl of 1 to 12 carbon atoms,
phenyl benzoates of the formula

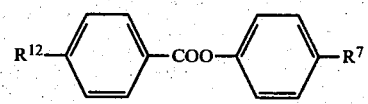

XXXII wherein $R^{12}$ is straight-chain alkyl of 1 to 8 carbon atoms or straight-chain alkanoyloxy of 2 to 9 carbon atoms and $R^7$ is as above,
p-(trans-4-alkylcyclohexyl)benzoic acid trans-4-alkylcyclohexyl esters of the formula

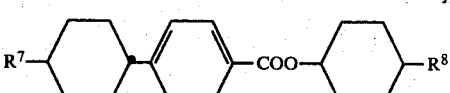

XXXIII wherein $R^7$ and $R^8$ are as above,
p-(trans-4-alkylcyclohexylcarbonyloxy)benzoic acid trans-4-alkylcyclohexyl esters of the formula

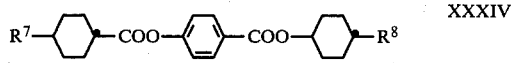

XXXIV wherein $R^7$ and $R^8$ are as above,
and/or trans-4-alkylcyclohexanecarboxylic acid trans-4-(p-alkylphenyl)cyclohexyl esters of the formula

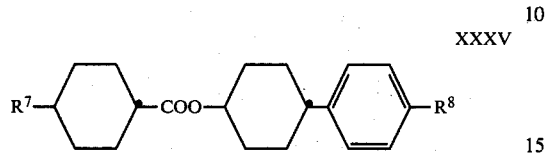

XXXV wherein $R^7$ and $R^8$ are as above.

The mixtures provided by the invention for the two-frequency control contain, one or more compounds of formula I.

The compounds of formulae XXII and XXXI hereinbefore are novel.

The compounds of formula XXII can be prepared by esterifying an acid of the formula $$A-COOH \qquad XXXVI$$

wherein A is a group of formulae XXIII or XXIV as described hereinbefore, $R^6$ is fluorine, chlorine or bromine and $R^5$—E has the significances given earlier, or a reactive derivative thereof with the compound of the formula

XXXVII

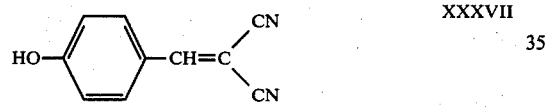

and, if desired, reacting a resulting compound of formula XXII in which A represents a group of formula XXIII and $R^6$ represents bromine with copper (I) cyanide, sodium cyanide or potassium cyanide.

The esterification of an acid of formula XXXVI or of a reactive derivative thereof (e.g. acid chloride or anhydride) with the phenol of formula XXXVII can be carried out in a manner known per se. Preferred methods are, insofar as A represents a group of formula XXIII, the reaction of the acid chloride (which can be obtained from the acid of formula XXXVI, for example, by heating with thionyl chloride) with the phenol of formula XXXVII and, insofar as A represents a group of formula XXIV, the reaction of the acid of formula XXXVI with the phenol of formula XXXVII in the presence of 4-(dimethylamino)pyridine and N,N'-dicyclohexylcarbodiimide. The reaction of a compound of formula XXII in which A represents a group of formula XXIII and $R^6$ represents bromine to give the corresponding compound in which $R^6$ represents cyano can also be carried out in a manner known per se. The reaction with copper (I) cyanide in dimethylformamide is preferred.

The compounds of formula XXXVI in which A represents a group of formula XXIII and $R^5$—E represents p-alkylphenyl or trans-4-alkylcyclohexyl are known compounds or are analogues of known compounds. The remaining compounds of formula XXXVI, i.e. those in which A represents a group of formula XXIII and $R^5$—E represents 4'-alkyl-4-biphenylyl, p-(trans-4-alkylcyclohexyl)phenyl or p-(5-alkyl-2-pyrimidinyl)-phenyl and those in which A represents a group of formula XXIV are on the other hand novel. They possess for the most part liquid crystalline properties also.

The compounds of formula XXXVI in which A represents a group of formula XXIII can be obtained according to Reaction Scheme 1 hereinafter in which $X^1$ represents fluorine, chlorine or bromine and $R^5$—E has the significances given earlier:

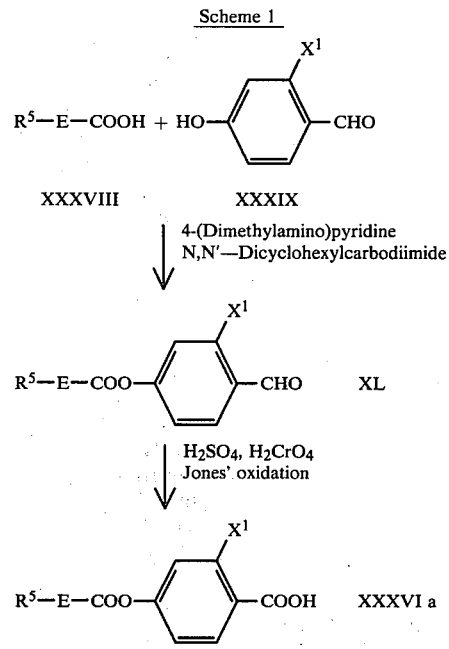

The acids of formula XXXVI in which A represents a group of formula XXIV can be prepared in a manner known per se by subjecting the known, liquid crystalline p-(5-alkyl-2-pyrimidinyl)benzonitriles to saponification (e.g. by heating with potassium hydroxide in ethylene glycol and subsequent addition of a mineral acid).

The compounds of formula XXXI can be prepared by reducing a compound of the formula

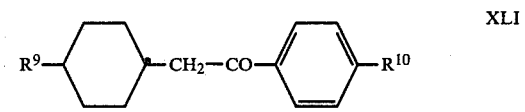

XLI wherein $R^9$ and $R^{10}$ have the significances given earlier, in a manner known per se; for example, by Clemmensen reduction or with hydrazine according to the Huang-Minlon process. The compounds of formula XLI can be obtained by Friedel-Crafts acylation of an alkyl- or alkoxybenzene with the acid chloride of a (trans-4-alkylcyclohexyl)acetic acid.

The mixtures provided by the invention with negative dielectric anisotropy conveniently contain in addition to one or more compounds of formula I one or more other compounds with negative and/or small positive anisotropy of the dielectric constants (compounds with positive dielectric anisotropy may be used in the application discussed here in accordance with definition only in amounts which do not leave the anisotropy of the total mixture positive), preferably a nematic compound or mixture having a dielectric anisotropy of at most about +1. Examples of preferred mixture components are the 2,3-dicyano-hydroquinone derivatives described in German Offenlegungsschrift No. 29 37 700 (U.S. Pat. No. 4,279,770) and the compounds of formulae XXV–XXXV hereinbefore.

The amount of the compounds of formula I in the mixtures provided by the invention can lie between about 1 and about 70 mol percent, preferably between about 10 and about 40 mol percent.

The mixtures in accordance with the invention can contain, in addition, optically active compounds (e.g. optically active biphenyls) and/or dichroic colouring substances (e.g. azo, azoxy or anthraquinone colouring substances). The amount of such compounds is determined by the solubility and the desired pitch, colour, extinction and the like. However, the amount of optically active compounds and colouring substances generally lies in each case between about 0.1 to about 10 mol percent. Of course, such additives can, however, also be absent.

The manufacture of the liquid crystalline mixtures provided by the invention can be carried out in a manner known per se; for example, by heating a mixture of the components to a temperature barely above the clearing point and subsequently cooling down.

The manufacture of an electro-optical device containing one or more compounds of formula I can also be carried out in a manner known per se; for example, by evacuating a suitable cell and introducing the corresonding compound or mixture into the evacuated cell.

The invention is also concerned with all novel compounds, mixtures, processes, uses and devices as herein described.

The following non-limiting Examples 1–4 illustrate the preparation of the compounds of formula I in accordance with the invention. Unless othewise stated, percentages and ratios are given in volume and the temperatures are expressed in degrees Centigrade. Room temperature is about 23° C. and the ether is diethyl ether. C signifies crystalline, S signifies smectic, N signifies nematic, Ch signifies cholesteric and I signifies isotropic phase. The transition points are also denoted correspondingly (e.g., N-I for the clearing points of a nematic liquid crystal). Unless otherwise indicated, the Examples were actually performed as written.

EXAMPLE 1

32.0 g of aluminium chloride were suspended in 150 ml of methylene chloride in a sulphonation flask with stirrer, gas inlet tube, low temperature thermometer, reflux condenser, dropping funnel and nitrogen gasification, cooled to 0° C. and then 43.3 g of trans-4-pentylcyclohexanecarboxylic acid chloride were added dropwise at 0° to 10° C. within 10 minutes. The mixture was stirred for a further 30 minutes while introducing nitrogen, then cooled to −10° C. and ethylene was introduced up to saturation. After completion of the reaction (about 3 hours), the excess ethylene was driven off with nitrogen and the batch was hydrolyzed by (dropwise at the beginning) addition of 70 ml of 1 N hydrochloric acid so that the internal temperature did not rise above 20° C. (strong cooling required). After separation of the organic phase, the aqueous solution was extracted with 100 ml of methylene chloride. The combined organic phases were washed with 150 ml of water, dried over sodium sulphate and concentrated at 30° C. on a rotary evaporator. The yellow coloured crude product obtained was recrystallized from 50 ml of ethanol at −20° C. Yield: 31.15 g (64%) of white crystals of 1-(trans-4-pentylcyclohexyl)-3-chloropropan-1-one; m.p. 42°–43° C.; Rf value (chloroform) 0.63.

EXAMPLE 2

(a) 48.9 g of 1-(trans-4-pentylcyclohexyl)-3-chloropropan-1-one (prepared according to Example 1) were dissolved in 350 ml of acetone in a round flask with reflux condenser and nitrogen gasification, 30.0 g of sodium iodide were added and the mixture was boiled at reflux for 1 hour. After cooling to room temperature, the mixture was concentrated on a rotary evaporator, the residue was taken up in 450 ml of absolute methanol and, after adding 14.3 g of potassium cyanide (spontaneous decolourization of the solution), the mixture was boiled at reflux for 2 hours. After cooling to room temperature, the solvent was evaporated, the residue was taken up in 350 ml of diethyl ether and washed twice with 150 ml of semi-concentrated sodium chloride solution each time. The aqueous phases were each back-extracted twice with 70 ml of diethyl ether. The combined organic phases were dried over sodium sulphate and evaporated to dryness. Recrystallization from 40 ml of ethyl acetate gave 27.25 g of white crystals. A further 8.75 g of white crystals were obtained by concentration of the mother liquor and recrystallization of the residue from 20 ml of hexane. Total yield: 36.0 g (76.6%) of γ-oxo-γ-(trans-4-pentylcyclohexyl)butyronitrile; m.p. 45°–46° C.; Rf value (chloroform) 0.45.

(b) 36.0 g of γ-oxo-γ-(trans-4-pentylcyclohexyl)-butyronitrile were dissolved in 400 ml of methanol in a sulphonation flask with stirrer, thermometer, dropping funnel and reflux condenser and a solution of 34.5 g of potassium hydroxide in 40 ml of water and 100 ml of methanol was added dropwise within 10 minutes. The mixture was subsequently boiled at reflux for 18 hours, cooled to room temperature and the solvent was removed on a rotary evaporator. The residue was taken up in 300 ml of water, acidified with 75 ml of concentrated hydrochloric acid and extracted firstly with 350 ml of methylene chloride and then with 150 ml of methylene chloride. The combined organic phases were washed twice with 200 ml of concentrated sodium chloride solution each time, dried over sodium sulphate and concentrated on a rotary evaporator. The light red coloured product was recrystallized from a solution of 120 ml of hexane and 110 ml of methylene chloride at −20° C., 27.8 g of white crystals being obtained. A further 2.4 g of crystals were obtained by concentration of the mother liquor and recrystallization of the residue from 50 ml of hexane and 30 ml of methylene chloride. Total yield: 30.2 g (77.2%) of γ-oxo-γ-(trans-4-pentylcyclohexyl)butyric acid; m.p. 113°–114° C.; Rf value (chloroform/acetone 2:1) 0.58.

(c) 56.6 g of γ-oxo-γ-(trans-4-pentylcyclohexyl)-butyric acid were dissolved in 500 ml of absolute ethanol in a sulphonation flask with stirrer, thermometer and reflux condenser, treated with 25 ml of hydrazine hydrate and boiled at reflux for 1.25 hours. After cooling to room temperature, the mixture was diluted with 750 ml of water, the separated precipitate was filtered off under suction, washed with a large amount of water and the still moist residue was crystallized from 80 ml of absolute ethanol at −20° C. Yield: 48.7 g (87.4%) of white crystals of 6-(trans-4-pentylcyclohexyl)-4,5-dihydro-3(2H)-pyridazinone; m.p. 152°–153° C.; Rf value (chloroform/acetone 2:1) 0.46.

(d) 47.5 g of 6-(trans-4-pentylcyclohexyl)-4,5-dihydro-3-(2H)-pyridazinone were dissolved in 140 ml of glacial acetic acid in a sulphonation flask with stirrer, thermometer, reflux condenser and dropping funnel and heated to 60° C. 33.4 g of bromine were subsequently added dropwise within 45 minutes, whereby a slight exothermic reaction set in immediately and further heating could accordingly be dispensed with. A white precipitate formed after a short time. After completion of the bromine addition, the mixture was stirred at 60° C. for a further 2 hours, then cooled to room temperature, the yellow coloured precipitate was filtered off under suction and washed with 200 ml of cold ethyl acetate. The almost white suction filter material was stirred well in 150 ml of dilute ammonia, suction filtered and washed with a large amount of water. The well pressed-out, still moist suction filter material was dissolved in 100 ml of hot absolute ethanol and filtered and then brought to crystallization by slowly cooling to −20° C., 41.8 g of white crystals being obtained. Concentration of the mother liquor and recrystallization of the residue from 10 ml of absolute ethanol gave a further 2.1 g of crystals. Total yield: 43.9 g (93%) of 6-(trans-4-pentylcyclohexyl)-3(2H)-pyridazinone; m.p. 124°–127° C.; Rf value (chloroform/acetone 2:1) 0.34.

(e) 19.85 g of 6-(trans-4-pentylcyclohexyl)-3(2H)-pyridazinone were suspended in 80 ml of absolute benzene at 30° C. in a sulphonation flask with stirrer, thermometer, reflux condenser and dropping funnel and 24.6 g of phosphorous oxychloride were added dropwise while stirring well within 30 minutes, whereby immediately an exothermic reaction and hydrogen chloride evolution set in and the temperature rose to 45° C. The temperature was subsequently increased slowly to 80° C. and the mixture was stirred at this temperature for 4 hours. After cooling to room temperature, the clear dark brown mixture was poured on to 200 g of ice, the benzene phase was separated and the aqueous phase was extracted twice with 100 ml of diethyl ether each time. The combined organic phases were washed with 100 ml of saturated sodium hydrogen carbonate solution and 100 ml of water (the aqueous phases were back-extracted with a small amount of diethyl ether), dried over sodium sulphate and evaporated. The brown coloured residue was recrystallized from 15 ml of methylene chloride and 15 ml of hexane at −20° C. There were obtained 9.1 g of white crystals which were washed well with hexane cooled to −20° C. Concentration of the mother liquor and recrystallization of the residue from 20 ml of hexane gave a further 7.25 g of white crystals. Total yield: 16.35 g (76.7%) of 3-chloro-6-(trans-4-pentylcyclohexyl)pyridazine; m.p. 81°–89° C.; Rf value (chloroform/acetone 2:1) 0.7.

EXAMPLE 3

16.0 g of 3-(trimethylsilylethynyl)-6-(trans-4-pentylcyclohexyl)pyridazine and 150 ml of methanol were placed in a flask under nitrogen and then 49 ml of 1 N potassium hydroxide were added dropwise within 20 minutes. Subsequently, the mixture was stirred at 40° C. for a further 30 minutes and then concentrated on a rotary evaporator. The residue was taken up in 150 ml of methylene chloride and washed three times with 150 ml of saturated sodium chloride solution each time. The wash solutions were back-extracted twice with 150 ml of methylene chloride each time. The organic phases were combined, dried with sodium sulphate, filtered and concentrated on a rotary evaporator. There were obtained 12.35 g of white crystals. Recrystallization from 100 ml of hexane and 20 ml of ethyl acetate gave 10.8 g (86.4%) of 3-ethynyl-6-(trans-4-pentylcyclohexyl)pyridazine as white crystals of melting point 114°–116° C.

The 3-(trimethylsilylethynyl)-6-(trans-4-pentylcyclohexyl)pyridazine used as the starting material was prepared as follows:

(a) 24.8 g of 6-(trans-4-pentylcyclohexyl)-3(2H)-pyridazinone (prepared according to Example 2) and 150 ml of toluene were suspended in a sulphonation flask under nitrogen. Subsequently, there was added dropwise within 7 minutes a solution of 11.5 g of phosphorus oxybromide, the temperature rising from 17° C. to 30° C. and a viscous light brown mass resulting. The mixture was treated with 30 ml of toluene and then heated slowly to 68° C., whereby it became dark green in colour. After 2 hours, a solution of 5.7 g of phosphorus oxybromide was added dropwise at 68° C. within 10 minutes. The mixture was heated to reflux temperature and once more treated with a solution of 7.4 g of phosphorus oxybromide. After 6 hours, the mixture was poured into 400 ml of ice/water and extracted six times with 250 ml of methylene chloride each time. The organic phases were washed with 400 ml of 5% sodium hydrogen carbonate solution, subsequently combined, dried with sodium sulphate and concentrated at 40° C. on a rotary evaporator. Column chromatography on silica gel with ethyl acetate/hexane (1:1) as the eluant gave 24.81 g of crude product. Crystallization from 75 ml of ethyl acetate/hexane (2:1) and working-up of the mother liquor finally yielded a total of 21.7 g of 3-bromo-6-(trans-4-pentylcyclohexyl)pyridazine as white crystals of melting point 101°–103° C.

(b) 17.1 g of 3-bromo-6-(trans-4-pentylcyclohexyl)pyridazine were suspended in 150 ml of triethylamine in a sulphonation flask under nitrogen. Subsequently, the suspension was treated with 772 mg of bis-(triphenylphosphine)-palladium (II) dichloride and 105 mg of copper (I) iodide and then 6.75 g of ethynyltrimethylsilane were added dropwise at room temperature within 5 minutes. The yellow mixture was stirred at room temperature for a further 2 hours, then at 32°–38° C. for 2 hours and subsequently at room temperature for a further 14 hours. Subsequently, the brown suspension was filtered, back-washed with methylene chloride and the filtrate was concentrated at 40° C. on a rotary evaporator. The residue was taken up in 150 ml of methylene chloride and washed once with 150 ml of semi-saturated sodium hydrogen carbonate solution and twice with 150 ml of water each time. The wash-waters were back-extracted twice with 150 ml of methylene chloride each time. The organic phases were combined, dried with sodium sulphate, filtered and concentrated on a rotary evaporator. Column chromatography of the resulting crude product (20.6 g) on silica gel with ethyl acetate/hexane (1:9) as the eluant yielded 16.93 g of light yellow crystals. Crystallization from 200 ml of hexane/ethyl acetate (9:1) and working-up of the mother liquor gave a total of 13.5 g (74.6%) of 3-(trimethylsilylethynyl)-6-(trans-4-pentylcyclohexyl)pyridazine as white crystals of melting point 118°–119° C.

EXAMPLE 4

2.56 g of 3-ethynyl-6-(trans-4-pentylcyclohexyl)-pyridazine were dissolved in 25 ml of tetrahydrofuran under nitrogen. The solution was cooled to −70° C. and then 7.5 ml of a 1.6 M solution of butyl lithium in hexane were added dropwise within 20 minutes. The mixture was stirred at −70° C. for a further 1 hour and then 0.74 ml of methyl iodide was added dropwise within 5 minutes. The mixture was stirred overnight and warmed slowly to room temperature. After 15.5 hours, the dark mixture was poured into 100 ml of water and made neutral with solid ammonium chloride. The solution obtained was extracted three times with 100 ml of ether each time. The ether phases were washed twice with 100 ml of water each time, subsequently combined, dried with sodium sulphate, filtered and concentrated on a rotary evaporator. Recrystallization of the resulting dark crystals in ethyl acetate/hexane (1:9) gave 1.87 g (70%) of 3-(1-propynyl)-6-(trans-4-pentylcyclohexyl)-pyridazine as brown crystals of melting point 103°–104° C. and clearing point (S-I) 99.3° C.

The following compound can be manufactured in an analogous manner:

3-(1-Pentynyl)-6-(trans-4-pentylcyclohexyl)pyridazine; m.p. 89.1° C.

I claim:

1. A compound of the formula

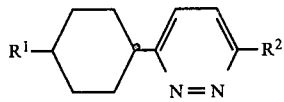

wherein $R^1$ is straight-chain alkyl of 1 to 12 carbon atoms, $R^2$ is 1-alkynyl and said 1-alkynyl group in $R^2$ is a straight-chain group of 2 to 10 carbon atoms.

2. The compound of claim 1 wherein the 1-alkynyl group in $R^2$ is a straight-chain group of 2 to 7 carbon atoms.

3. The compound of claim 1 wherein $R^1$ is straight-chain alkyl of 3 to 9 carbon atoms.

4. The compound of claim 3 wherein $R^1$ is straight-chain alkyl of 3 to 7 carbon atoms.

5. The compound of claim 1 wherein $R^1$ is straight-chain alkyl of 3 to 7 carbon atoms and $R^2$ is straight-chain 1-alkynyl of 2 to 7 carbon atoms.

6. The compound of claim 1, 3-ethynyl-6-(trans-4-pentylcyclohexyl)pyridazine.

7. The compound of claim 1, 3-(1-propynyl)-6-(trans-4-pentylcyclohexyl)pyridazine.

8. The compound of claim 1, 3-(1-pentynyl)-6-(trans-4-pentylcyclohexyl)pyridazine.

9. An electro-optical cell having two plate means at least one plate means being transparent; means for controlling the optical activity of the cell; and liquid crystal means including a compound of the formula

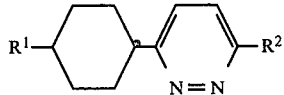

wherein $R^1$ is straight-chain alkyl of 1 to 12 carbon atoms, $R^2$ is 1-alkynyl and said 1-alkynyl group in $R^2$ is a straight-chain group of 2 to 10 carbon atoms.

10. A liquid crystal mixture comprising a compound of the formula

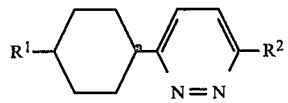

wherein $R^1$ is straight-chain alkyl of 1 to 12 carbon atoms, $R^2$ is 1-alkynyl and said 1-alkynyl group in $R^2$ is a straight-chain group of 2 to 10 carbon atoms.

11. The liquid crystal mixture of claim 10 wherein the dielectric anisotropy of the total mixture is negative.

12. The liquid crystal mixture of claim 10 comprising
(a) a compound of the formula

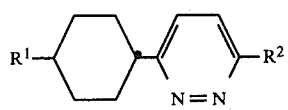

wherein $R^1$ is straight-chain alkyl of 1 to 12 carbon atoms, $R^2$ is 1-alkynyl and said 1-alkynyl group in $R^2$ is a straight-chain group of 2 to 10 carbon atoms; and (b) a nematic compound or mixture having a dielectric anisotropy of at most about +1.

13. The liquid crystal mixture of claim 12 comprising
(a) a compound of the formula

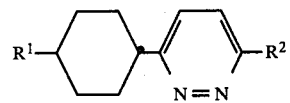

wherein $R^1$ is straight-chain alkyl of 1 to 12 carbon atoms, $R^2$ is 1-alkynyl and said 1-alkynyl group in $R^2$ is a straight-chain group of 2 to 10 carbon atoms;

(b) a nematic compound or mixture having a dielectric anisotropy of about −3 to +1; and (c) a compound or mixture having a cross-over frequency of about 100 Hz to about 20 kHz and having a positive dielectric anisotropy of more than about 10 at frequencies below the cross-over frequency of the total mixture.

14. The liquid crystal mixture of claim 12 wherein said nematic compound or mixture having a dielectric anisotropy of at most about +1 is one or more compounds selected from the group consisting of

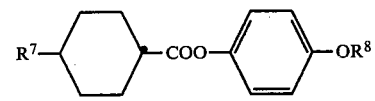

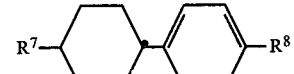

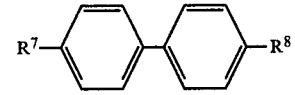

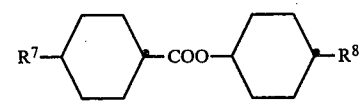

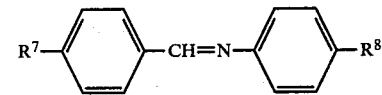

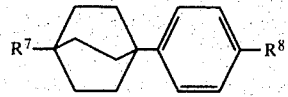
XXX wherein, in each of formulas XXV through XXX, $R^7$ and $R^8$ each are straight-chain alkyl of 1 to 8 carbon atoms

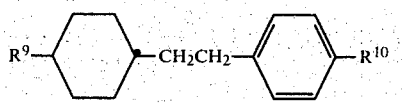
XXXI wherein $R^{10}$ is $-R^{11}$ or $-OR^{11}$ and $R^9$ and $R^{11}$ each are straight-chain alkyl of 1 to 12 carbon atoms

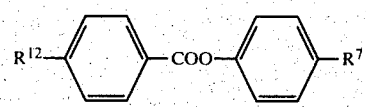
XXXII wherein $R^{12}$ is straight-chain alkyl of 1 to 8 carbon atoms or straight-chain alkanoyloxy of 2 to 9 carbon atoms and $R^7$ is straight-chain alkyl of 1 to 8 carbon atoms

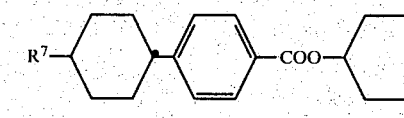
XXXIII

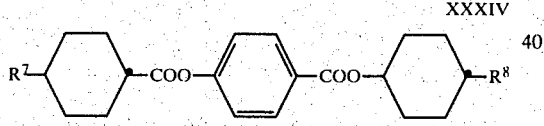
XXXIV and

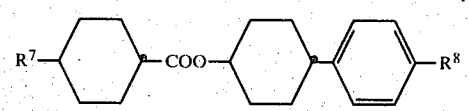
XXXV wherein, in each of formulas XXXIII through XXXV, $R^7$ and $R^8$ each are straight-chain alkyl of 1 to 8 carbon atoms.

15. The liquid crystal mixture of claim 13 wherein said compound or mixture having a cross-over frequency of about 100 Hz to about 20 kHz and a dielectric anisotropy of more than about 10 is:
a compound of the formula

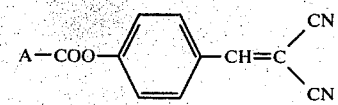
XXII wherein A represents a group of the formula

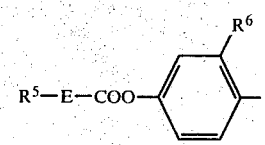
XXIII or

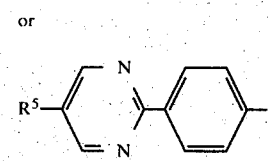
XXIV wherein $R^5$ alone is straight-chain alkyl of 1 to 12 carbom atoms and $R^6$ is fluorine, chlorine, bromine or cyano and $R^5$—E is p-alkylphenyl, trans-4-alkylcyclohexyl, 4'-alkyl-4-biphenylyl, p-(trans-4-alkylcyclohexyl)phenyl or p-(5-alkyl-2-pyrimidinyl)phenyl.

* * * * *